(12) United States Patent
Mayle et al.

(10) Patent No.: US 11,291,570 B2
(45) Date of Patent: Apr. 5, 2022

(54) HYBRID STENT AND DELIVERY SYSTEM

(71) Applicant: Cook Medical Technologies LLC, Bloomington, IN (US)

(72) Inventors: Brent A. Mayle, Spencer, IN (US); Ram H. Paul, Jr., Bloomington, IN (US); James C. Merk, Terre Haute, IN (US); Gary Neff, Blomington, IN (US); Dean R. Puckett, Bloomfield, IN (US); Austin Neidigh, Bloomfield, IN (US); Thomas Mindel, Bloomington, IN (US); Michelle Reynolds, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 109 days.

(21) Appl. No.: 16/393,268

(22) Filed: Apr. 24, 2019

(65) Prior Publication Data
US 2019/0328562 A1 Oct. 31, 2019

Related U.S. Application Data

(60) Provisional application No. 62/663,416, filed on Apr. 27, 2018.

(51) Int. Cl.
| | | |
|---|---|---|
| A61F 2/915 | (2013.01) | |
| A61F 2/958 | (2013.01) | |
| A61M 25/10 | (2013.01) | |

(52) U.S. Cl.
CPC .............. *A61F 2/915* (2013.01); *A61F 2/958* (2013.01); *A61F 2002/9155* (2013.01); *A61F 2220/0025* (2013.01); *A61M 25/1002* (2013.01)

(58) Field of Classification Search
CPC .. A61F 2/958; A61F 2/915; A61F 2/86; A61F 2/90; A61F 2002/9155; A61F 2220/0025; A61F 2250/0048; A61F 2002/91575; A61F 2/962; A61M 25/1002
See application file for complete search history.

(56) References Cited

U.S. PATENT DOCUMENTS

| | | |
|---|---|---|
| 4,484,955 A | 11/1984 | Hochstein |
| 4,902,508 A | 2/1990 | Badylak et al. |
| 5,383,892 A | 1/1995 | Cardon et al. |
| 5,387,235 A | 2/1995 | Chuter |
| 5,632,762 A | 5/1997 | Myler |

(Continued)

FOREIGN PATENT DOCUMENTS

| | | |
|---|---|---|
| CA | 2468670 A1 | 6/2003 |
| EP | 1 138 280 A2 | 10/2001 |

(Continued)

OTHER PUBLICATIONS

Extended European Search Report and Opnion of EP 19 17 1696, dated Jul. 22, 2019.

(Continued)

*Primary Examiner* — Sarah A Simpson
(74) *Attorney, Agent, or Firm* — Crowell & Moring LLP (57) ABSTRACT

Disclosed herein is a hybrid stent having a balloon-expandable portion joined to a self-expanding portion. The hybrid stent is capable of withstanding the forces applied by delivery. Delivery systems for deploying a hybrid stent are described, as are methods of using such delivery systems.

22 Claims, 5 Drawing Sheets

(56) References Cited

U.S. PATENT DOCUMENTS

| | | |
|---|---|---|
| 5,711,969 A | 1/1998 | Patel et al. |
| 5,720,776 A | 2/1998 | Chuter et al. |
| 5,733,337 A | 3/1998 | Carr, Jr. et al. |
| 5,817,126 A | 10/1998 | Imran |
| 5,885,619 A | 3/1999 | Patel et al. |
| 5,955,110 A | 9/1999 | Patel et al. |
| 5,968,069 A | 10/1999 | Dusbabek et al. |
| 5,968,096 A | 10/1999 | Whitson et al. |
| 5,984,955 A | 11/1999 | Wisselink |
| 6,168,621 B1 | 1/2001 | Vrba |
| 6,206,931 B1 | 3/2001 | Cook et al. |
| 6,293,955 B1 | 9/2001 | Houser et al. |
| 6,325,820 B1 | 12/2001 | Khosravi et al. |
| 6,485,507 B1 | 11/2002 | Walak et al. |
| 6,514,285 B1 | 2/2003 | Pinchasik |
| 6,582,461 B1 | 6/2003 | Burmeister et al. |
| 6,626,937 B1 | 9/2003 | Cox |
| 6,652,576 B1 | 11/2003 | Stalker |
| 6,699,277 B1 | 3/2004 | Freidberg et al. |
| 6,716,238 B2 | 4/2004 | Elliott et al. |
| 6,740,113 B2 | 5/2004 | Vrba |
| 6,830,575 B2 | 12/2004 | Stenzel et al. |
| 6,890,350 B1 | 5/2005 | Walak |
| 6,911,040 B2 | 6/2005 | Johnson et al. |
| 6,923,829 B2 | 8/2005 | Boyle et al. |
| 6,945,994 B2 | 9/2005 | Austin et al. |
| 6,964,681 B2 | 11/2005 | Murray, III et al. |
| 7,037,327 B2 | 5/2006 | Salmon |
| 7,175,652 B2 | 2/2007 | Cook et al. |
| 7,175,655 B1 | 2/2007 | Molaei |
| 7,225,518 B2 | 6/2007 | Eidenschink et al. |
| 7,238,197 B2 | 7/2007 | Sequin et al. |
| 7,285,130 B2 | 10/2007 | Austin |
| 7,393,358 B2 | 7/2008 | Malewicz |
| 7,470,282 B2 | 12/2008 | Shelso |
| 7,632,302 B2 | 12/2009 | Vreeman et al. |
| 7,632,303 B1 | 12/2009 | Stalker et al. |
| 7,758,634 B2 | 7/2010 | Brucker et al. |
| 7,955,370 B2 | 6/2011 | Gunderson |
| 8,012,192 B2 | 9/2011 | Eidenschink et al. |
| 8,016,872 B2 | 9/2011 | Parker |
| 8,025,694 B2 | 9/2011 | Strauss et al. |
| 8,308,798 B2 | 11/2012 | Pintor et al. |
| 8,562,666 B2 | 10/2013 | Bonsignore |
| 8,679,171 B2 | 3/2014 | Deem et al. |
| 8,734,501 B2 | 5/2014 | Hartley et al. |
| 8,894,701 B2 | 11/2014 | Vad |
| 8,936,634 B2 | 1/2015 | Irwin et al. |
| 9,248,016 B2 | 2/2016 | Oba et al. |
| 9,675,481 B2 | 6/2017 | Vad |
| 9,943,422 B2 | 4/2018 | Hartley et al. |
| 10,195,059 B2 | 2/2019 | Hartley et al. |
| 2001/0016766 A1 | 8/2001 | Vardi et al. |
| 2001/0053129 A1 | 12/2001 | Vonesh et al. |
| 2002/0007102 A1 | 1/2002 | Salmon et al. |
| 2002/0198587 A1 | 12/2002 | Greenberg et al. |
| 2002/0198588 A1 | 12/2002 | Armstrong et al. |
| 2003/0105513 A1 | 6/2003 | Moriuchi |
| 2003/0120332 A1 | 6/2003 | Hartley |
| 2003/0195609 A1 | 10/2003 | Berenstein et al. |
| 2004/0054396 A1 | 3/2004 | Hartley et al. |
| 2004/0073289 A1 | 4/2004 | Hartley |
| 2004/0082990 A1 | 4/2004 | Hartley |
| 2004/0098079 A1 | 5/2004 | Hartley et al. |
| 2004/0106978 A1 | 6/2004 | Greenberg et al. |
| 2004/0236414 A1 | 11/2004 | Brar et al. |
| 2005/0004647 A1 | 1/2005 | Bassoe |
| 2005/0131519 A1 | 6/2005 | Hartley |
| 2006/0074403 A1 | 4/2006 | Rafiee |
| 2006/0173529 A1* | 8/2006 | Blank ............... A61F 2/91 623/1.16 |
| 2006/0241740 A1 | 10/2006 | Vardi et al. |
| 2007/0005126 A1 | 1/2007 | Tischler |
| 2007/0043418 A1 | 2/2007 | Lee et al. |
| 2007/0219618 A1 | 9/2007 | Cully |
| 2007/0293940 A1 | 12/2007 | Schaeffer et al. |
| 2009/0005848 A1 | 1/2009 | Strauss et al. |
| 2009/0018643 A1 | 1/2009 | Hashi et al. |
| 2009/0043377 A1 | 2/2009 | Greenberg et al. |
| 2009/0125095 A1 | 5/2009 | Bui et al. |
| 2009/0210048 A1 | 8/2009 | Amplatz |
| 2009/0210049 A1 | 8/2009 | Thielen |
| 2009/0306766 A1* | 12/2009 | McDermott ............. A61F 2/88 623/1.16 |
| 2009/0319023 A1* | 12/2009 | Hildebrand ............. A61F 2/07 623/1.13 |
| 2011/0152760 A1 | 6/2011 | Parker |
| 2011/0152994 A1 | 6/2011 | Hendriksen |
| 2011/0172762 A1 | 7/2011 | Hartley et al. |
| 2011/0265908 A1 | 11/2011 | Clerc |
| 2012/0029624 A1 | 2/2012 | Dierking |
| 2013/0018451 A1 | 1/2013 | Grabowski et al. |
| 2013/0023977 A1 | 1/2013 | Kumazawa et al. |
| 2013/0325141 A1 | 12/2013 | Gill et al. |
| 2015/0232975 A1 | 8/2015 | Tofail |
| 2016/0158036 A1 | 6/2016 | Loganathan |
| 2017/0027682 A1 | 2/2017 | Merk et al. |
| 2017/0071768 A1* | 3/2017 | Krieger ............... A61F 2/844 |
| 2019/0069986 A1* | 3/2019 | Lukas ................. A61F 2/07 |
| 2019/0328561 A1 | 10/2019 | Mayle et al. |
| 2019/0328562 A1 | 10/2019 | Mayle et al. |

FOREIGN PATENT DOCUMENTS

| | | |
|---|---|---|
| EP | 1 138 280 A3 | 1/2004 |
| WO | WO 98/22158 A1 | 5/1998 |
| WO | WO 98/53761 A1 | 12/1998 |
| WO | WO 99/29262 A1 | 6/1999 |
| WO | WO 02/030329 A2 | 4/2002 |
| WO | WO 2002/066095 A2 | 8/2002 |
| WO | WO 03/034948 A1 | 5/2003 |
| WO | WO 03/053287 A1 | 7/2003 |
| WO | WO 2003063729 | 8/2003 |
| WO | WO 03/082153 A2 | 10/2003 |
| WO | WO 2004/002365 A1 | 1/2004 |
| WO | WO 2004/002370 A1 | 1/2004 |
| WO | WO 2004/017867 A1 | 3/2004 |
| WO | WO 2004/028399 A2 | 4/2004 |
| WO | WO 2009144463 | 12/2009 |
| WO | WO 2015/141399 A1 | 9/2015 |

OTHER PUBLICATIONS

Humpston, Giles, et al., "Principles of Soldering", Jan. 1, 2004 (Jan. 1, 2004), XP055607673. Retrieved from the internet: URL:https://www.asminternational.org/documents/10192/1849770/06244G_Frontmatter.pdf [retrieved on Jul. 22, 2019].

Duwuri, S., "A single-step stent delivery, deployment, and expansion system," Cathet Cardiovasc Diagn. Mar. 1997, 40(3): 308-10.

Georgiadis, G., "Hybrid endografts combinations for the treatment of endoleak in endovascular abdominal aortic aneurysm repair," Int J Artif Organs, 2012.

Pyng, L., "Airway Stents," Clin Chest Med 31 (2010) 141-150.

Extended European Search Report—EP 19171687.7-1113, dated Jul. 30, 2019 (9 pages).

European Patent Office Communication for European Application No. 04794819.5 dated Jun. 20, 2013 (5 pages).

European Patent Office Communication for European Application No. 04794819.5 dated Apr. 9, 2014 (5 pages).

European Patent Office Communication for European Application No. 04794819.5 dated Dec. 17, 2014 (4 pages).

Extended European Search Report for European Application No. 16197983.6, dated Feb. 16, 2017, pp. 1-7.

International Search Report for corresponding PCT/US2004/033567 dated Jul. 2, 2005 (4 pages).

Partial European Search Report for European Application No. 12275210.8, dated Jun. 14, 2013, pp. 1-6.

Scurr, R.H. James et al., "Fenestrated Stent-Graft Repair: Which (56) References Cited

OTHER PUBLICATIONS

Stent Should Be Used to Secure Target Vessel Fenestrations?," *J of Endovascular Therapy* (2008) pp. 344-348.

* cited by examiner

HYBRID STENT AND DELIVERY SYSTEM

BACKGROUND

The present application generally relates to medical devices. More particularly, the present application relates to stents and delivery systems for stents.

Stents of different construction have been used to treat a variety of conditions. When stiffness is desired, a balloon-expandable (BX) stent is sometimes selected, as its shape can be set during deployment by application of an inflation force from a balloon of the delivery system. In applications for treatment more tortuous anatomy, a self-expanding (SX) stent may be desired for its relative flexibility.

Hybrid stents combining balloon-expandable and self-expanding sections have been contemplated in the art, but none are available in the market owing to the fact that construction of a hybrid stent which performs as desired is a major challenge. First, the materials used to construct balloon-expandable and self-expanding sections are generally dissimilar, and conventional joining methods are likely to fail. Second, during deployment, a stent is subjected to various forces from the delivery system. The forces experienced by a balloon-expandable stent are different from those experienced by an self-expanding stent, which can endanger the survival of the joint between the two sections, assuming the two can be joined in the first place.

Certain medical implants include balloon-expandable and self-expanding stents in a single device. Among these are fenestrated stent grafts, in which a balloon-expandable stent is disposed through the fenestration of the main body of the stent graft, and an self-expanding stent extends as the body of a side branch, extending away from the main body into a branch vessel. In such an instance, the self-expanding stent is joined to the balloon-expandable stent via graft material.

Because of the varied forces that need to be applied to and withstood by the device, it may be beneficial to develop delivery systems which are capable of delivering a hybrid stent having a balloon-expandable portion and an self-expanding portion. Such a device would allow for the expansion of the self-expanding portion while providing a balloon for expansion of the balloon-expandable portion. Additionally, such a device may be useful in the delivery of standard self-expanding stents, as current methods involve delivery and implantation with a first system which carries the device within the vasculature, the withdrawal of that delivery system, and the provision of a second system to the implantation site, which carries a balloon to affect a dilatation step in which the implant is patent with the vessel wall.

It has been a challenge to develop a hybrid stent which has a balloon-expandable portion and an self-expanding portion which can withstand delivery intact, and a delivery system capable of delivering such a stent. It has likewise been a challenge to provide a single delivery system and delivery method capable of delivering an self-expanding stent and dilating the self-expanding stent such that it is seated patent against the wall of the body vessel to which it has been delivered.

SUMMARY

In one aspect, the present disclosure provides a stent. The stent includes a tubular body which extends from a first end to a second end and defines a lumen therethrough. The tubular body may include a first portion extending from the first end to a third end. The first portion may be a self-expanding tubular body. The stent may include a second portion extending from the second end to a fourth end. The second portion may be a balloon-expandable tubular body. The stent may include an attachment selected from one of a rivet and a solder joint comprising at least two solders, the attachment joining the first portion to the second portion. The attachment may be capable of withstanding a total shearing force of about 20 newtons (N) applied during deployment from a delivery system, or a shearing force of about 0.1 N to about 0.5 N at each joint between the balloon-expandable portion and the self-expanding portion.

In another aspect, the present disclosure provides a method of making a stent. The method includes disposing a first flux onto an end of a self-expanding tubular body, and soldering to form a first coated portion. The method includes disposing a second flux onto an end of a balloon-expandable tubular body, and soldering to form a second coated portion. The first flux and the second flux are distinct from one another. The method may include contacting the first coated portion with the second coated portion. The method may further include heating the first coated portion and the second coated portion to join the self-expanding tubular body to the balloon-expandable tubular body, thereby forming the stent.

In another aspect, the present disclosure provides a medical device assembly. The medical device assembly includes a balloon catheter having a catheter body extending from a proximal end to a distal end and defining a lumen therethrough, and at least one inflatable balloon disposed circumferentially about a portion of the catheter body. The at least one inflatable balloon has an interior in fluid communication with the lumen of the catheter body. The medical device assembly includes a stent which may have a tubular body extending from a first end to a second end and defining a lumen therethrough. The tubular body may include a first portion extending from the first end to a third end. The first portion may be a self-expanding tubular body. The tubular body may include a second portion extending from the second end to a fourth end. The second portion may be a balloon-expandable tubular body. An attachment may join the first portion to the second portion. In the medical device assembly, at least the second portion of the stent being disposed over at least one inflatable balloon of the balloon catheter.

Further objects, features and advantages of this system will become readily apparent to persons skilled in the art after a review of the following description, with reference to the drawings and claims that are appended to and form a part of this specification.

DETAILED DESCRIPTION

The drawings are purely schematic illustrations of various aspects of the invention and are not necessarily to scale, unless expressly stated.

The terms "substantially" or "about" used herein with reference to a quantity includes variations in the recited quantity that are equivalent to the quantity recited, such as an amount that is equivalent to the quantity recited for an intended purpose or function. "Substantially" or derivatives thereof will be understood to mean significantly or in large part.

Figure 1:
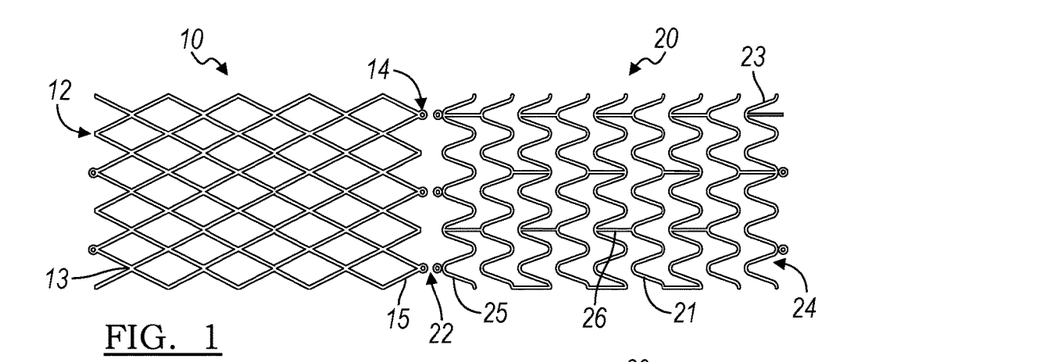
FIG. 1 is a plan view of a balloon-expandable stent portion and a self-expanding stent portion for construction of a hybrid stent in accordance with the principles of the present invention.

A hybrid stent may be made by joining a balloon-expandable stent to a self-expanding stent. As shown in FIG. 1, a balloon-expandable stent portion 10 extends from first end 12 to third end 14 to define a stent portion body 13. Likewise, a self-expanding stent portion 20 extends from a second end 22 to a fourth end 24, to define a stent portion body 23 therebetween.

Numerous designs are known in the art for a variety of balloon expandable and self-expanding stents. Although any known design of a stent is contemplated as being compatible as a stent portion with the principles of the present disclosure, those balloon expandable and self-expanding stent portions which are cut from a precursor cannula are particularly suited for such a purpose. Materials appropriate for precursor cannulas will be known by those of skill in the art.

For example, in one embodiment, the balloon expandable stent portion may be cut from a stainless steel cannula or one made of a cobalt chromium alloy, and the self-expanding stent portion 20 may be made from a shape memory metal, such as a nickel titanium alloy.

As shown in FIG. 1, the balloon expandable stent portion may have a closed cell structure. In other embodiments, the balloon-expandable stent portion may have a more open structure. In an embodiment, the self-expanding stent portion body 23 may be made up of a plurality of coaxial rings 25, which are in turn made up of a plurality of struts 21. The plurality of rings 25 may be connected via one or more connectors 26. As has been depicted in FIG. 1, the rings may be connected by a plurality of connectors 26, and these connectors 26 may be aligned axially along the length of the device 20. Such an arrangement may increase the column strength of the self-expanding stent portion 20 relative to other arrangements, and may assist in reducing shortening of the stent during deployment.

However, in other embodiments, it will be suitable to have connectors 26 arranged in a different relationship; that is, out of axial alignment.

Figure 2:
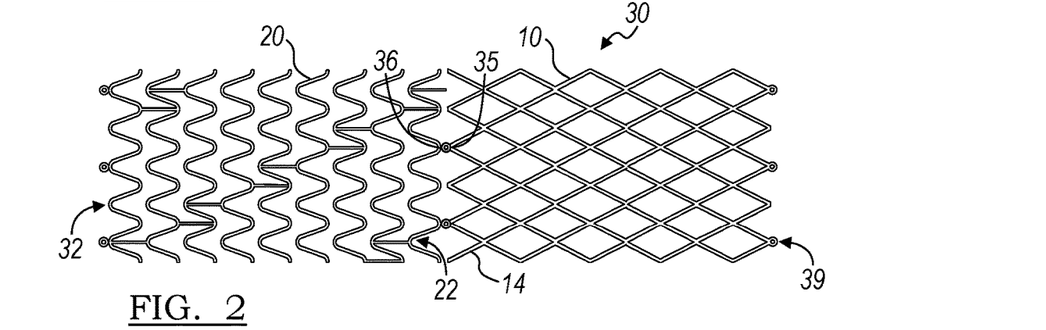
FIG. 2 is a hybrid stent constructed from a balloon-expandable stent portion and a self-expanding stent portion.

The balloon-expandable stent portion 10 can be joined to the self-expanding stent 20 to create a hybrid stent 30 as is shown in FIG. 2. In this Figure, third end 14 of the balloon-expandable stent portion 10 has been joined to second end 22 of the self-expanding stent portion, thereby resulting in the formation of junction 36. The hybrid stent 30 extends from first hybrid stent end 32 to second hybrid stent end 39, which are concurrent with fourth end 24 of the self-expanding stent portion and first end 12 of the balloon expandable stent portion, respectively. As will be apparent to one of skill in the art, other end-to-end to joining methods are possible in the construction of a hybrid stent.

In order to be delivered to the body vessel to be treated and to be an effective treatment, the hybrid stent 30 will ideally remain intact during and after delivery. The development of a hybrid stent has been difficult for this reason. The nature of the delivery system and the delivery procedure means that a number of forces will be applied to the stent; a compressive force from the outer sheath of the delivery system, for example, and axial forces of elongation (wherein the hybrid stent is stretched longer than its natural length, and the halves may be pulled apart) and an axial shearing force (wherein the balloon-expandable and self-expanding portions of the hybrid stent are compressed axially toward one another.) This shearing force is capable of breaking connections at the joints if the means of joining the balloon-expandable portion to the self-expanding portion is not sufficiently strong.

In some embodiments, the hybrid stent 30 is capable of withstanding a total shearing force of about 20 newtons (N) about the circumference of the device at the junction between the self-expanding and balloon-expandable portion. In some embodiments, each joint (such as each individual solder joint, or each rivet) at the junction between the self-expanding portion and the balloon-expandable portion is capable of withstanding about 0.1N to about 0.5N of shearing force, which is a local shearing force. The shearing force may be about applied locally to a unit of 0.03 mm$^2$ to any given portion of the hybrid stent. The shearing force is a translation of forces from the overall compressive forces measured in the stent for deployment that each element (including the joints at the junction of the balloon-expandable and self-expanding portions) is exposed to due to resistance associated with sliding the sheath over the stent for deployment.

The diameters of the self-expanding stent portion and the balloon expandable stent portion are substantially equal to one another in one embodiment. In another embodiment, one of the diameters may be slightly smaller than the other. For example, a balloon-expandable stent portion may have a smaller diameter in the expanded state than does the self-expanding stent portion, and an end of the balloon-expandable stent portion may be placed within the lumen of the self-expanding stent portion, thereby providing a contact point for joining the two and forming the hybrid stent. Moreover, the balloon-expandable stent and the hybrid stent may have different lengths. For instance, a longer self-expanding portion can be employed to create a longer overall stent.

In certain embodiments, the balloon-expandable stent portion 10 may be manufactured with a plurality of first eyelets 15 at at least one end, and likewise the self-expanding stent portion 20 may be manufactured with a plurality of second eyelets 25. If eyelets are provided, these may provide a suitable component at which the balloon-expandable stent portion 10 may be joined to the self-expanding stent portion 20. One or both of the devices may have eyelets, or, in another embodiment, neither device may have a plurality of eyelets. In the hybrid stent 30 depicted in FIG. 2, the first eyelets 15 are joined to second eyelets 25 to form a plurality of joined eyelets 35 at junction 36.

As mentioned previously, the balloon-expandable stent portion 10 may be made of a different material than the self-expanding stent portion 20. It can be challenging to join two dissimilar materials. In particular, if one of the two precursor stent portions is made of a shape memory alloy, it is known that these materials are difficult to manipulate, even without the additional complication of attempting to join to a dissimilar material.

Figure 3:
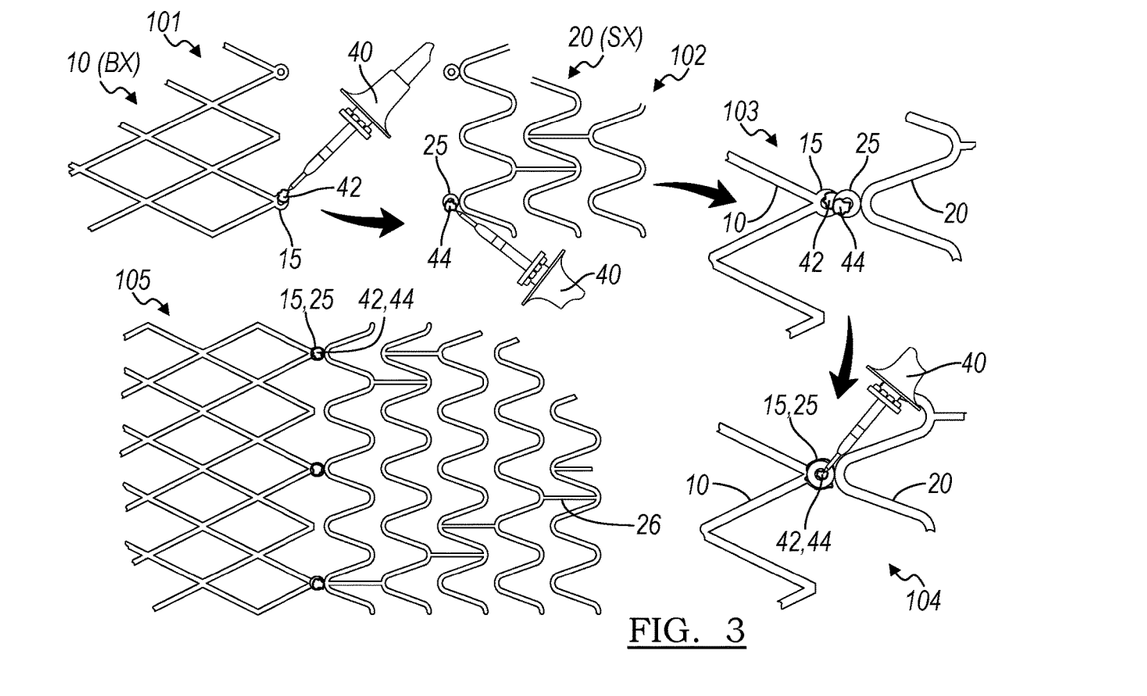
FIG. 3 illustrates steps in a method of construction of a hybrid stent in accordance with an aspect of the present disclosure.

One joining method is illustrated in FIG. 3. In a first step 101, a balloon-expandable stent portion 10 having a joining portion, such as plurality of eyelets 15, is provided. A first flux 42 compatible with the material from which the balloon-expandable stent portion 10 is made is deposited on the joining portion (eyelet 15), such as by brushing or by dipping. Then, solder is applied over the first flux is and allowed to set. Alternatively, the first flux 42 may be provided in conjunction with a solder (such as in the core of a solder wire) and may be provided using a soldering iron 40, as illustrated in FIG. 3.

Similarly, in step 102, a second flux 44 is applied to a joining portion of a self-expanding stent portion 20, in the illustrated case eyelets 25. The second flux 44 is then covered with solder. Therefore the material of the balloon-expandable stent portion 10 and of the self-expanding stent portion 20 are selected such that the first flux 42 and the second flux 44 are compatible with the materials of the two stent portions.

The first flux 42 may be used with a first solder, and the second flux 44 may be used with a second solder. The first solder may be different from the second solder, or the first solder may be the same as the second solder. The first flux 42 may be different from the second flux 44.

In a third step 103, the solder deposited on the balloon-expandable stent portion 10 is brought into contact with the solder deposited on the self-expanding stent portion 20.

In step 104, heat is applied to at least partially liquefy the solders of both stent portion. After a time, the heat is removed, and step 105 yields the hybrid stent 30 which is joined at the eyelets 15 and 25 by a single solder joint, making use of the two different fluxes.

In one example, the balloon expandable stent portion 10 may be made of stainless steel, and the self-expanding stent portion 20 may be made of a nickel-titanium alloy, such as NITINOL. A steel-compatible flux, such as STAY-CLEAN zinc chloride flux, may be used to cover a portion of the stainless steel stent portion, such as a stainless steel eyelet, and a titanium-compatible flux such as an acid-based solder not containing zinc or chlorine, and which can remove titanium and nickel oxides, may be used to cover a portion of the self-expanding stent portion, such as an eyelet. A solder compatible with both fluxes may then be used, such as ALLSTATE 430 soft silver solder. As mentioned, the solder and respective flux may be applied separately, or the solder and flux may be provided together.

Figure 4:
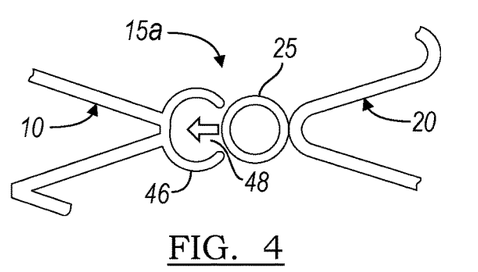
FIG. 4 is an embodiment of an interface of two stent portions in accordance with an aspect of the present disclosure.

If applied to two stents with a standard thickness along their entire lengths, the method of FIG. 3 will yield a hybrid stent 30 with a thickest portion at the junction 36. Therefore, a number of modifications to the eyelets are contemplated. As illustrated in FIG. 4, at least one of the eyelets (in this case, first eyelet 15a of the balloon-expandable stent portion 10) may be slit such that the eyelet 15a can have an open configuration 46. In the embodiment illustrated in FIG. 4, the slit is located on the circumference of the eyelet 15a at the extreme end of the device 10, but in other embodiments it may be formed anywhere on the eyelet 15a. The second eyelet 25 of the self-expanding stent portion 20 is a standard closed eyelet 25 which can be disposed such that it is circumferentially surrounded by the first eyelet 15a. The stents 10 and 20 can then be joined by any method to yield a hybrid stent 30.

Figure 5:
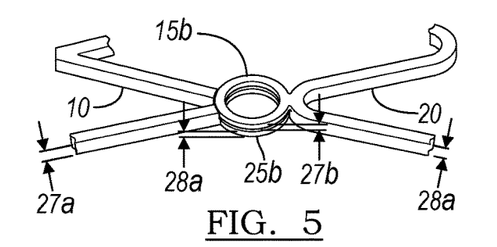
FIG. 5 is another embodiment of an interface between two stent portions in accordance with another aspect of the present disclosure.

In another embodiment, illustrated in FIG. 5, both the balloon-expandable stent portion 10 and the self-expanding stent portion 20 may have modified joining portions; in the illustrated embodiment, first eyelets 15a and second eyelets 15b. In this embodiment, the struts of the balloon-expandable stent portion 10 have a first thickness 27a, and the eyelet (or junction portion, or joining portion) has a second thickness 27b which is less than the first thickness 27a. Likewise, the self-expanding stent portion 20 has struts of a third thickness 28a, and the second eyelets a fourth thickness 28b less than the third thickness 28a. As such, the eyelets are thinned compared to the remainder of the device. In an environment in which the stent portion 10 or 20 is cut from a precursor cannula, this thinning may be achieved after the stent has been cut from the cannula, such as by electropolishing, or by another thinning method. This allows the hybrid stent 30 resulting from the joining of eyelet 15b to eyelet 25b to have a substantially consistent thickness across its entire length.

The self-expanding stent portion 20 may be joined to the balloon-expandable stent portion 10 by a number of different mechanisms. As already described, one such method includes using a flux compatible with the material of each stent, and then reheating such that two solders flowed over the flux can be joined. In some embodiments, the solders may be applied to eyelets of the stent portions, and may flow into the eyelets, as though to form a rivet made of solder through both eyelets of both stent portions of the hybrid stent.

Figure 6:
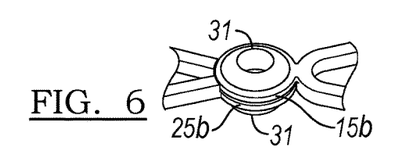
FIG. 6 is another embodiment of an interface between two stent portions in accordance with another aspect of the present disclosure.

FIG. 6 illustrates another type of connection that can be used to join a self-expanding stent portion 20 to a balloon-expandable stent portion 10 to manufacture a hybrid stent 30. In this environment, the eyelets are aligned in the radial dimension and a rivet 31 is disposed through both eyelets. The rivet 31 is then crimped down to join the balloon-expandable stent portion 10 to the self-expanding stent portion 20. The mechanical connection provided by a rivet 31 renders the junction 36 durable. A plurality of rivets 31 may be used to join some or all of the eyelets in such a paired fashion. In some embodiments, the rivet may be made of a pliable but radiopaque material, including but not limited to one of at least one of gold and platinum, in order to provide the device with a radiopaque marker for visualization during implantation, and monitoring of the implanted device.

Other methods may be used to attach the self-expanding and balloon-expandable portions of the hybrid stent, beyond soldering and rivets. For example, the two halves may be attached via a sonic weld, or a friction stir weld, or another joining method A hybrid stent may provide better sizing to a vessel in which it is implanted than a stent which is only balloon-expandable or self-expanding. A hybrid stent may have a controllable radial force profile, may ease positioning of the implant, and may minimize or eliminate stent jumping during deployment. The hybrid stent design may minimize jumping and increase accuracy in positioning because one portion of the device is delivered while the other remains within the delivery system.

A hybrid stent as disclosed herein may be of particular assistance in bridging a relatively straight vessel (using a balloon-expandable portion as an anchor) to a more tortuous vessel (taking advantage of the self-expanding portion). Such hybrid stents may be constructed with varying amounts of covering along their length. In one embodiment, both the balloon-expandable portion and the self-expanding portion may be completely covered by graft material. In another embodiment, only portions the balloon-expandable and self-expanding portions may be covered. In another embodiment, the hybrid stent may be a bare metal stent. In one example, treatment of a calcified ostial lesion may benefit from a balloon-expandable portion to hold open the lesion, and the flexibility of the self-expanding portion may provide a transition to the healthy part of the vessel.

Figure 7:
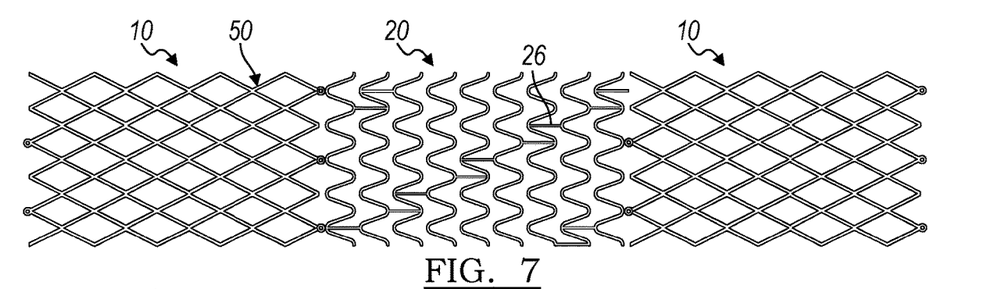
FIG. 7 is an embodiment of a hybrid stent having three sections in accordance with an aspect of the present disclosure.

The present disclosure is not limited to hybrid stents derived from the joining of a single balloon-expandable stent portion 10 to a single self-expanding stent portion 20. As shown in FIG. 7, a hybrid stent 50 may include more than two precursor stent portions. In the example illustrated in FIG. 7, a self-expanding stent portion 20 is positioned between two balloon expandable stents 10. Such a device may be particularly useful in an area of anatomy in which two vessels to be supported are bridged by a curved vessel. A hybrid stent 50 as in FIG. 7 could be used in a stent graft in a trauma application in which there is a transected vessel, wherein each balloon-expandable portion is positioned in a vessel end for securement of the device, and the central self-expanding portion bridges the two, allowing for a flexible central section.

Figure 8:
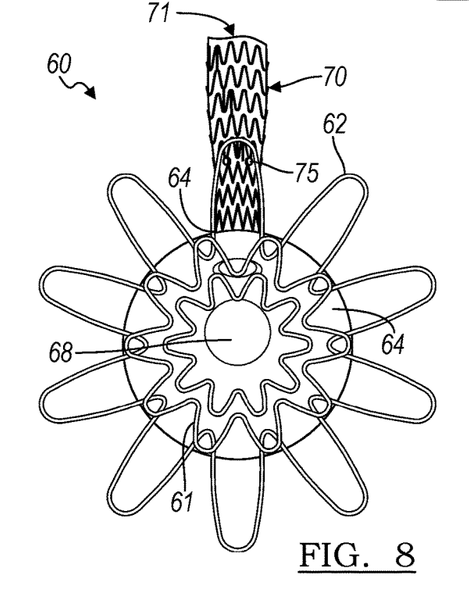
FIG. 8 is an end view of a stent graft constructed with a hybrid stent in accordance with an embodiment of the present disclosure.
Figure 9:
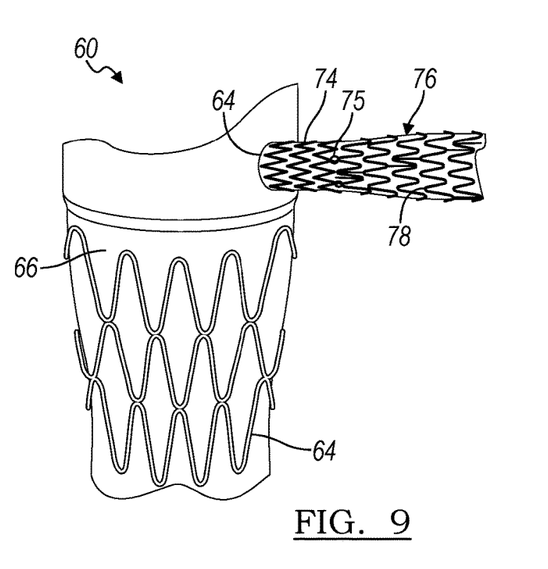
FIG. 9 is a side view of a portion of the stent graft of FIG. 8.

Hybrid stents constructed in accordance with the principles of the present invention are useful for a number of applications. Turning now to FIGS. 8 and 9, a stent graft 60 is depicted. Stent graft 60 is a fenestrated stent graft, having a main body 61 which has at least one fenestration 64 formed through the graft material 66, which defines the tubular shape of the main body 61. The hybrid stent 72 in this embodiment is a structural component of side branch 70, which engages with main body 61 at and through fenestration 64. In one embodiment, the hybrid stent 72 is held in place by flaring of the balloon-expandable portion within the main body 61 of the stent graft 60. The side branch 70 has a side branch lumen 71 formed therethrough, which is in fluid communication with the main body lumen 68 via fenestration 64.

The two stent portions of the hybrid stent 72 of side branch 70 serve different purposes. balloon-expandable portion 74 serves as a flaring portion, imparting stiffness to the construct and interacting with the fenestration 64. The self-expanding portion 76 extends away from the main body 61 and allows for more flexibility and conformation to the natural curvature of vessel into which the side branch 70 is to be deployed.

Various procedures may dictate how much covering or graft material is used in a variety of portions of a stent graft in embodiments of the present disclosure. In some instances, the hybrid stent may be utilized as a bare metal stent. In other embodiments, the hybrid stent may be fully covered with a graft material. In still other embodiments, the hybrid stent may be partially covered, with covering over a portion of the stent and exposed metal at other portions along its length. The balloon-expandable and self-expanding stents making up such a hybrid stent for use in a stent graft may also be constructed at a variety of diameters, and may have a variety of coverings along their lengths.

The graft material 66 used in a stent graft 60 may be a tubular graft material, and may be non-porous so that it does not leak or sweat under physiologic forces. The graft material may be made of a biocompatible material, including but not limited to a DACRON® polyester, another polyester fabric, polytetrafluoroethylene (PTFE), expanded PTFE, THORALON®, a polyamide, and other synthetic materials known to those of skill in the art. Naturally occurring biomaterials, such as collagen, particularly a derived collagen material known as extracellular matrix (ECM), such as small intestinal submucosa (SIS), may also be employed. In some embodiments, the graft material may be constructed as a preshaped tube. In some embodiments, the graft material may be a woven material.

In some embodiments, a stent graft including a hybrid stent in accordance with the principles of the present disclosure may be constructed to have a smooth covering, such as one which is described in U.S. patent application Ser. No. 15/224,101, the entire contents of which are incorporated herein by reference.

A stent graft (or hybrid stent) constructed in accordance with the principles of the present invention may be suitable for number of applications. One such application is the transjugular intrahepatic portosystemic shunt (TIPS) procedure. In TIPS, an artificial channel within the liver is created to establish communication between the inflow portal vein and the outflow hepatic vein in order to treat, among other conditions, portal hypertension. This procedure is currently conducted with multiple devices, or a single non-hybrid stent. A hybrid stent or a stent graft including a hybrid stent may be delivered to the liver, in some embodiments over a wire guide, such that the distal end of the hybrid stent protruding from the liver and into portal vein would be a self-expanding portion, and the proximal section spanning the tract newly formed in the liver would be the balloon-expandable portion.

The use of a hybrid stent in a TIPS procedure may provide a number of advantages over present methodologies. First, the use of preselected precursor devices provides zoned diameter targets, and allow for a tunable gradient of pressure by selecting appropriate precursor stent portions from which to make the hybrid device. Moreover, the combination of a balloon-expandable portion and an self-expanding portion into a single hybrid device facilitates easy deployment of the hybrid device, while leaving a stiff device in place to shunt across the diseased liver. In addition, because the balloon-expandable portion can be manipulated by multiple balloon dilatations, the hybrid stent would have an adjustable character, allowing for a better fit within the anatomy.

FIGS. 10-13 illustrate views of delivery systems which may be used to deliver and implant a hybrid stent as described herein. Such delivery systems may facilitate a multistep deployment scheme while making use of a single delivery system to be introduced to the body. A person of ordinary skill in the art will be aware that the dimensions of such a system may be tailored to the use of the particular device.

As mentioned, both balloon expandable and self-expanding stents are delivered to an implantation site in the lumen of a body vessel by specialized equipment which is tailored to the particular type of stent to be used. FIGS. 10 through 13 illustrate a number of embodiments of delivery systems which are suitable for delivering a hybrid stent that includes at least one self-expanding section and at least one balloon expandable section. A person of ordinary skill in the art will also appreciate that certain of these delivery systems may be suitable for delivering a self-expanding stent only, or a balloon expandable stent only.

Figure 10:
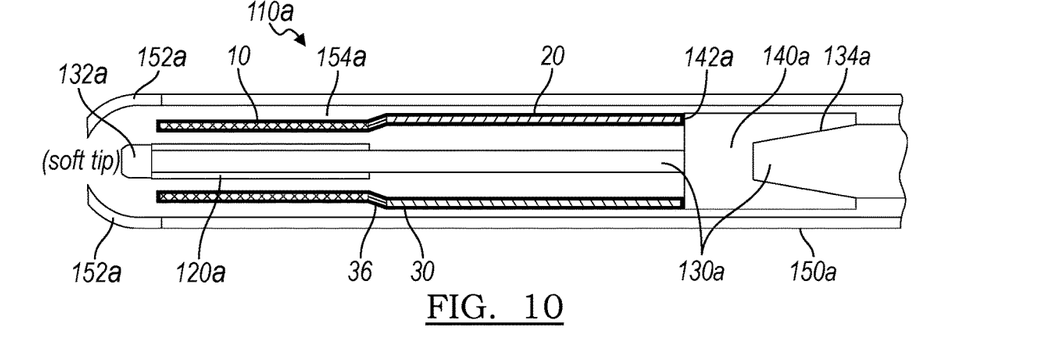
FIG. 10 is a cross-sectional view of an embodiment of a delivery system constructed in accordance with an embodiment of the present disclosure.

Delivery system 110a, as shown in FIG. 10, Includes an inner catheter 130a which is a balloon catheter. The hybrid stent 30 in this embodiment is disposed over the inner catheter 130a, with the balloon expandable portion 10 disposed or crimped over balloon 120a, and the self-expanding portion 20 compressed within outer sheath 150a over a section of inner catheter 130a which does not include the balloon 128. The balloon-expandable portion 10 may be crimped to a diameter such that it is in contact with the balloon 120a, or it may be slightly larger than this so that it does not contact the balloon, as illustrated in FIG. 10. The junction 36 is the portion of hybrid stent 30 which lies between the balloon-expandable stent portion 10 and the self-expanding stent portion 20. The outer sheath 150a may optionally have at its distal end a flexible section 152a, which provides a delivery configuration in which the delivery system 110a is more compact, but also allows for straightforward ejection of the implant (hybrid stent 30) when the delivery system reaches the treatment site.

The inner catheter 130a likewise has at its distal end a soft tip 132a. At least one of soft tip 132a and flexible section 152a may further be embedded with radiopaque particles, or made of a radiopaque polymer, such that the delivery system may be tracked through the vasculature by known visualization methods, such as fluoroscopy. In the illustrated embodiment, the inner catheter 130a may have a smaller diameter in a distal section over which the stent is to be compressed and delivered, and may have a larger diameter in a portion proximal of this.

As shown in FIG. 10, the inner catheter 130a may include a taper 134a as its diameter narrows to the lower profile toward the distal end. Optionally, a pusher element 140 may be provided with, or provided surrounding, the inner catheter 140a. The pusher element 140a, in the illustrated embodiment, provides a contact face 142a, which is in contact with the second end 39 of the hybrid stent 30. In the illustrated embodiment, the second end 39 is an end of the self-expanding stent portion 20.

In other embodiments, the delivery system 110a may not include a pusher element 140, as the crimped down section of the balloon-expandable stent portion 10 may provide sufficient anchoring such that the implant does not slide when the inner catheter 130a or the outer sheath 150a is moved, thereby further allowing for a decrease in profile of the delivery assembly 110a.

Figure 11:
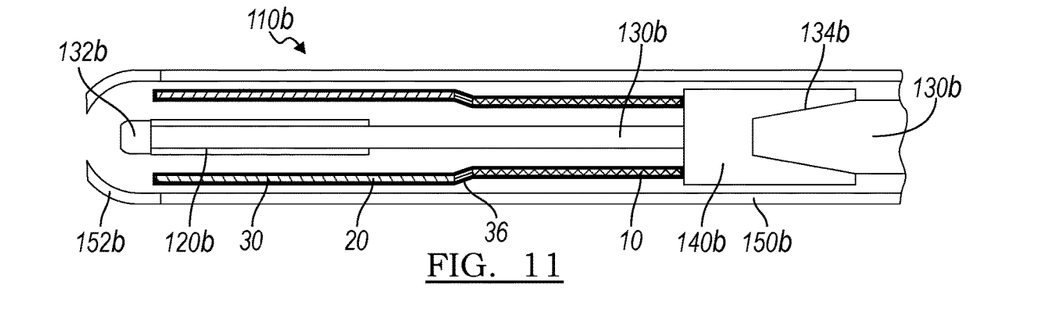
FIG. 11 is a cross-sectional view of another embodiment of a delivery system constructed in accordance with an embodiment of the present disclosure.

FIG. 11 illustrates a delivery assembly 110b, which is another delivery assembly which can be used in accordance with the principles of the present disclosure. In this embodiment, the self-expanding portion of the hybrid stent 30 exits the delivery sheet 150b first, in contrast to the embodiment illustrated in FIG. 10, in which the balloon expandable portion of the hybrid stent 30 exits the delivery system 110a first. In this embodiment, the components of the outer sheath 150b and the inner catheter 130b are largely arranged as they are in the embodiment of FIG. 10, with the balloon being positioned distally and adjacent the distal tip 132b, and the self-expanding stent portion 20 of the hybrid stent 30 being effectively delivered over the balloon of the balloon catheter.

Figure 14:
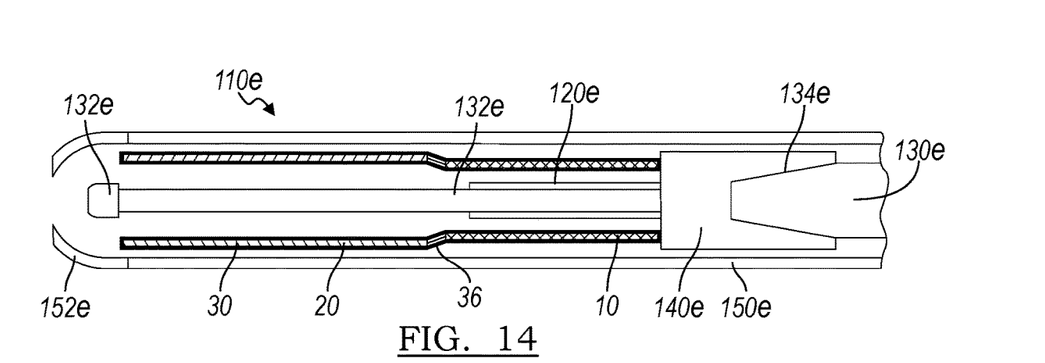
FIG. 14 is a cross-sectional view of another embodiment of a delivery system constructed in accordance with an embodiment of the present disclosure.
Figure 15A:
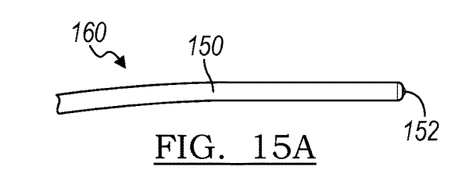
FIGS. 15A, 15B, 15C, and 15D are steps in the release of a hybrid stent from a sheath in accordance with an embodiment of the present disclosure.
Figure 15B:
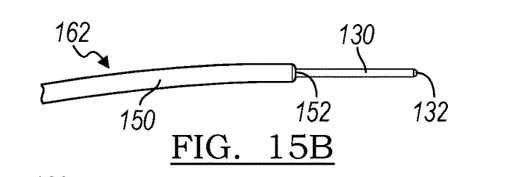
Figure 15C:
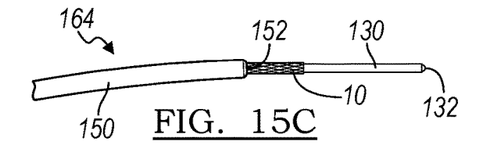
Figure 15D:
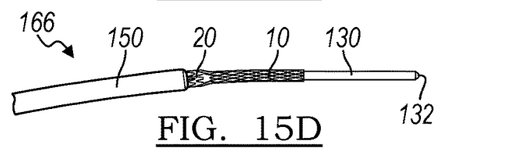
Figure 16A:
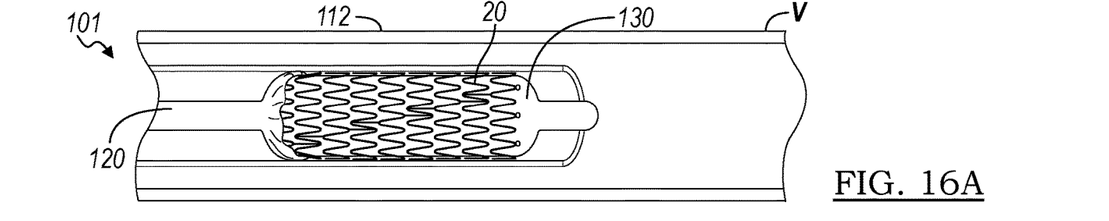
FIGS. 16A, 16B, 16C, and 16D are steps in the delivery of a hybrid stent using a wedge element in accordance with another embodiment of the present disclosure.
Figure 16B:
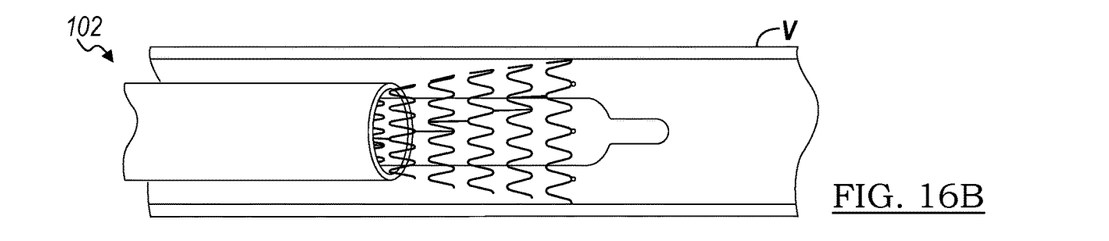
Figure 16C:
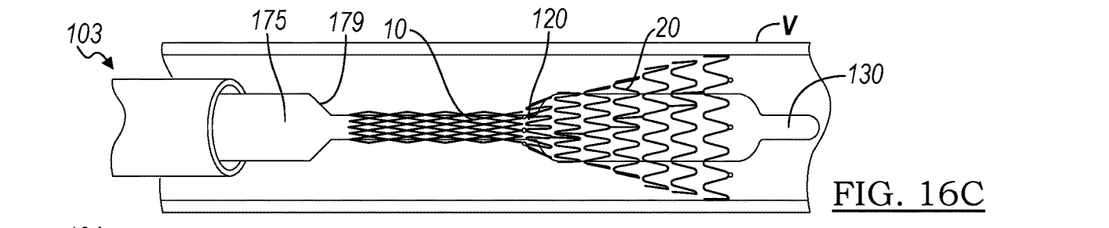
Figure 16D:
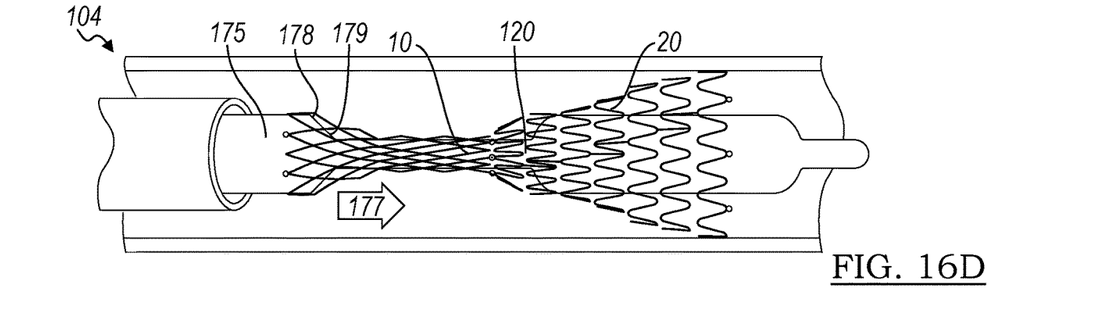

In another related embodiment, shown in FIG. 14, the positioning of the balloon 120e may be changed, such that the balloon expandable portion 10 is delivered over the balloon 120e.

In some embodiments, the balloon-expandable portion 10 may be crimped over the balloon 120b/120e. In embodiments where the balloon expandable portion 10 is crimped over the balloon 120b/120e, the delivery assembly 110b/110e may be provided without a pusher band 140b/140e, as the crimped balloon-expandable stent portion 10 may provide axial stability for the device to be delivered within the delivery assembly 110b/110e.

Figure 12:
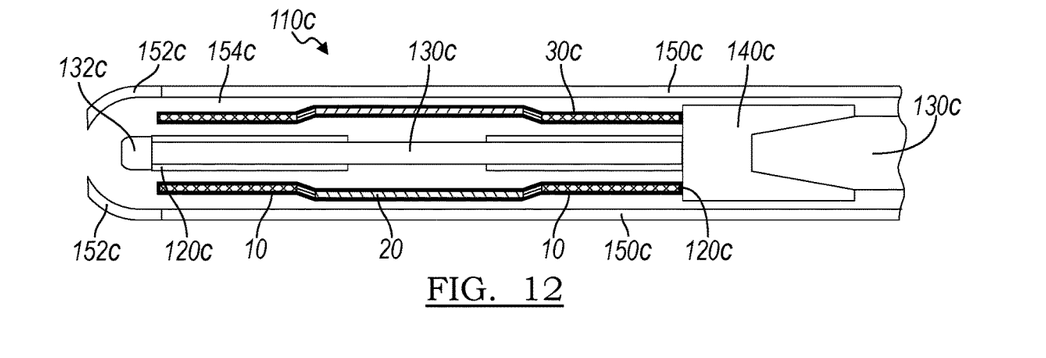
FIG. 12 is a cross-sectional view of another embodiment of a delivery system constructed in accordance with an embodiment of the present disclosure.

In FIG. 12, another embodiment of a delivery assembly 110c is illustrated. In this embodiment, the hybrid stent 130c includes three portions: two balloon expandable stents 10 at the proximal and distal ends of the hybrid stent 30C, and a self-expanding stent portion 20 bridging the two balloon expandable stent portions 10. In this embodiment, the inner catheter 130c is provided with two balloons 120c. The two balloon expandable portions 10 are each disposed over one of the balloons 120c. As in the foregoing examples if the balloon-expandable portion is disposed over a balloon in the delivery configuration, the delivery assembly may be provided without pusher 140c. In one embodiment, each of the balloons is provided with a separate inflation lumen for the delivery of inflation fluid; in another embodiment, the two balloons may share a common inflation lumen. A number of variations on this design are possible. For example, the two balloons maybe sized differently in the case that the diameters the final diameter of the different from one another in order to facilitate a size match with the anatomy, or to compensate for varying vessel size.

In some embodiments, a multiballoon delivery system may have two different expanded diameters. For instance, in one example the balloon-expandable portion of the hybrid stent may be an 8 millimeter (mm) diameter stent, and may be crimped over a 3 mm balloon. In this case, the 3 mm balloon may be inflated to slightly expand the balloon-expandable portion, and the delivery system may also provide an 8 mm balloon. After the initial expansion, the 8 mm balloon may be moved within the balloon-expandable portion of the stent and fully expanded to deploy the hybrid device. If a hybrid stent has multiple balloon-expandable portions, a delivery system of this design may have multiple 3 mm balloons, corresponding to the number of balloon-expandable portions.

Figure 13:
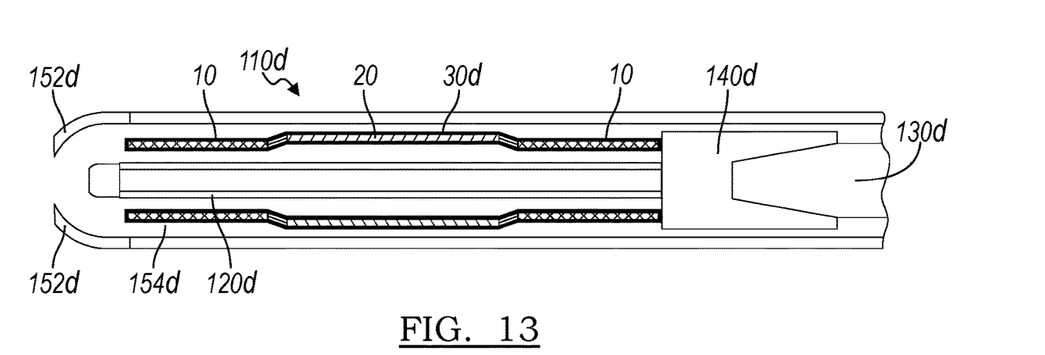
FIG. 13 is a cross-sectional view of another embodiment of a delivery system constructed in accordance with an embodiment of the present disclosure.

Alternatively, having a balloon expandable segment 10 at each end and a self-expanding segment bridging the middle of the device may be delivered with the delivery system 120d as depicted in FIG. 13. In this embodiment, rather than two small balloons as in FIG. 12, a single balloon running the length of the entire implant is provided. As above, the balloon combined with the crimped balloon expandable stents could take the place of, or work in accordance with, a pusher band 140d.

In an alternative to the embodiments in which multiple balloons are employed, a single balloon having a plurality of different folded and/or expanded diameters along its length may instead be substituted, thereby offering the ability to have differing final diameters of the crimped and/or expanded stent portions associated with these portions. These teachings may be applied to the embodiments illustrated in FIGS. 10-14.

FIGS. 15A through 15D and 16A through 16D illustrate steps in the delivery of a hybrid stent in accordance with another embodiment of the present disclosure. These figures are directed to embodiments of delivery systems which offer a decreased circumferential profile for delivery to smaller vessels. In each of these embodiments, the balloon expandable portion 10 may be crimped over the catheter at a position that is not over a balloon. In one embodiment, the balloon expandable portion may be crimped distal the balloon, as shown in FIGS. 15A to 15D; in another embodiment, the balloon-expandable portion may be crimped proximal the balloon as shown in FIGS. 16A through 16D.

In the embodiment illustrated in FIGS. 15A through 15D, the balloon expandable portion 10 of hybrid stent 30 may be crimped distal of the balloon 120. Provided in the assembly and disposed over the inner catheter 130 is tapered sleeve 170, which has at its distal end a taper 174. This taper 174 may take the shape of a frustoconical section at the distal end of the sleeve 170, with the smallest diameter of the taper 174 being at the distal end of the sleeve 170 and the diameter increasing proximally. This taper 174 may function as a wedge, when the sleeve 170, which is disposed over the inner catheter 130, is moved distally through the interior of the balloon expandable portion 10, thereby slightly expanding the diameter of the balloon expandable portion 10 from its crimped condition. This then allows for relative movement of the inner catheter so that the balloon 120 may expand the balloon expandable portion 10 at the site of treatment, when the balloon 120 is inflated.

In one delivery method with a wedge element, and in which the balloon-expandable portion is deployed to the vessel first, the self-expanding portion may be contained within the sheath 150 to act as an anchor to prevent the entire hybrid stent from moving out of the proper location for deployment. The outer sheath can then be retracted in steps in which the balloon-expandable portion can be exposed one to two segments or cells at a time, and the inner balloon catheter and the wedge (in one embodiment, a 3 mm wedge) located proximal to the balloon can be pulled proximally into the exposed cells. This can be repeated 1-2 cells at a time until the balloon-expandable portion is completely exposed and slightly expanded. Following this, an 8 mm balloon positioned proximal of the wedge could be placed into the slightly-expanded stent for inflation to 8 mm. This process can be repeated for each balloon-expandable portion of a hybrid stent having multiple balloon-expandable portions. One of skill in the art will appreciate that the dimensions of a delivery system and a device as described herein can vary based on the application.

Likewise, in the embodiment illustrated in FIGS. 16A through 16D, the balloon expandable portion 10 may be crimped proximal of the balloon 120. In this embodiment, the self-expanding portion may be positioned over the balloon 120 of the inner catheter 130. In a similar way, tapered sleeve 175 is disposed over, and axially movable relative to, inner catheter 130. The tapered sleeve 175 includes a taper 179 which, when driven through the interior of the balloon expandable portion 10 by movement 177, expands to a partially expanded configuration 178. As in the examples of FIGS. 15A-15D, the balloon may then be positioned within the interior of the balloon expandable portion, and inflated.

As a person skilled in the art will readily appreciate, the above description is only meant as an illustration of implementation of the principles this application. This description is not intended to limit the scope of this application in that the system is susceptible to modification, variation and change, without departing from the spirit of this application, as defined in the following claims.

What is claimed is:

1. A stent comprising: a tubular body extending from a first end to a fourth end and defining a lumen therethrough, the tubular body comprising: a first portion extending from the first end to a third end, the first portion comprising a balloon-expandable tubular body; a second portion extending from a second end to the fourth end, the second portion comprising a self-expanding tubular body; and an attachment selected from one of a rivet and a solder joint comprising at least two fluxes, the attachment joining the first portion to the second portion at a plurality of attachment points, wherein the plurality of attachment points are configured to withstand a shearing force of about 0.1 newton to about 0.5 newton at each of the plurality of attachment points applied during deployment from a delivery system.

2. The stent of claim 1, wherein the attachment joins the third end to the second end.

3. The stent of claim 1, wherein the attachment comprises a first solder and a second solder.

4. The stent of claim 1, wherein the third end has a thickness in a radial dimension less than a thickness of the remainder of the first portion.

5. The stent of claim 1, wherein the third end and the second end each comprise at least one eyelet.

6. The stent of claim 5, wherein the stent comprises a rivet disposed through at least one eyelet of the third end and at least one eyelet of the second end.

7. The stent of claim 6, wherein the rivet comprises a radiopaque material.

8. The stent of claim 1, wherein the second portion comprises a plurality of rings each comprising a plurality of struts and bends, and a plurality of connectors, each connector extending from one ring to a corresponding adjacent ring.

9. The stent of claim 8, wherein the bends of the plurality of rings have an in-phase relationship, and wherein each connector is axially aligned with at least one other connector.

10. The stent of claim 1, wherein the tubular body is at least partly covered by a graft material.

11. The stent of claim 1, wherein the attachment is capable of withstanding a shearing force of about 0.5 newton at each of the plurality of attachment points.

12. A medical device assembly comprising: a balloon catheter comprising: a catheter body extending from a proximal end to a distal end and defining a lumen therethrough, and at least one inflatable balloon disposed circumferentially about a portion of the catheter body, the at least one inflatable balloon having an interior in fluid communication with the lumen of the catheter body; and a stent comprising: a tubular body extending from a first end to a fourth end and defining a lumen therethrough, the tubular body comprising: a first portion extending from the first end to a third end, the first portion comprising a balloon-expandable tubular body; a second portion extending from a second end to the fourth end, the second portion comprising a self-expanding tubular body; and an attachment selected from one of a rivet and a solder joint comprising at least two fluxes, the attachment joining the first portion to the second portion at a plurality of attachment points, wherein the plurality of attachment points are configured to withstand a shearing force of about 0.1 newton to about 0.5 newton at each of the plurality of attachment points applied during deployment from a delivery system.

13. The medical device assembly of claim 12, wherein the inflatable balloon extends through a lumen of the first portion.

14. The medical device assembly of claim 12, wherein the attachment joins the third end to the fourth end.

15. A hybrid stent comprising: a tubular body extending from a first end to a fourth end and defining a lumen therethrough, the tubular body comprising:
- a first stent portion extending from the first end to a third end, the first stent portion comprising a balloon-expandable tubular body of a first material;
- a second stent portion extending from a second end to the fourth end, the second stent portion comprising a self-expanding tubular body of a second material different from the first material; and
- a joining portion between the first stent portion and the second stent portion selected from one of a rivet and a solder joint comprising at least two fluxes, the joining portion joining the first stent portion to the second stent portion at a plurality of attachment points, wherein the plurality of attachment points are configured to withstand a shearing force of about 0.1 newton to about 0.5 newton at each of the plurality of attachment points applied during deployment from a delivery system.

16. The hybrid stent of claim 15, wherein one of the first and second stent portions comprises a shape memory alloy and the other of the first and second stent portions comprises stainless steel.

17. The hybrid stent of claim 16, wherein the first stent portion comprises stainless steel and the second stent portion comprises a nickel titanium alloy.

18. The hybrid stent of claim 15, wherein the joining portion comprises a plurality of first eyelets at the third end and a plurality of second eyelets at the second end.

19. The hybrid stent of claim 18, wherein the first stent portion comprises a plurality of struts having a thickness and the second stent portion comprises a plurality of struts having a thickness, and the plurality of first eyelets at the third end comprise a thickness and the plurality of second eyelets at the second end comprise a thickness, wherein the thickness of the plurality of first eyelets at the third end is less than the thickness of the plurality of struts of the first stent portion and the thickness of the plurality of second eyelets at the second end is less than the thickness of the plurality of struts of the second stent portion.

20. They hybrid stent of claim 18, wherein the plurality of first eyelets at the third end and the plurality of second eyelets at the second end are aligned in a radial dimension and a rivet is disposed through each of a pair of eyelets.

21. The hybrid stent of claim 15, wherein the joining portion comprises a solder joint comprising two fluxes, wherein the two fluxes are compatible with the first material and the second material.

22. The hybrid stent of claim 15, wherein a first flux of the two fluxes is different from a second flux of the two fluxes.

* * * * *